(12) United States Patent
Kato et al.

(10) Patent No.: US 8,182,481 B2
(45) Date of Patent: May 22, 2012

(54) PFO CLOSING DEVICE

(75) Inventors: Yukitoshi Kato, Hadano (JP); Yasushi Iida, Ashigarakami-gun (JP); Takahiko Kawahara, Hadano (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 894 days.

(21) Appl. No.: 12/200,539

(22) Filed: Aug. 28, 2008

(65) Prior Publication Data

US 2009/0076525 A1 Mar. 19, 2009

Related U.S. Application Data

(60) Provisional application No. 60/976,130, filed on Sep. 28, 2007.

(30) Foreign Application Priority Data

Aug. 28, 2007 (JP) .................................. 2007-221905

(51) Int. Cl.
*A61B 18/12* (2006.01)

(52) U.S. Cl. ............... 606/49; 606/41; 606/50; 606/213

(58) Field of Classification Search .................. 606/41, 606/45–50, 213–216
See application file for complete search history.

(56) References Cited

U.S. PATENT DOCUMENTS

| | | | |
|---|---|---|---|
| 5,507,744 A | 4/1996 | Tay et al. | |
| 5,709,224 A | 1/1998 | Behl et al. | |
| 5,810,810 A | 9/1998 | Tay et al. | |
| 5,827,268 A | 10/1998 | Laufer | |
| 5,919,200 A | 7/1999 | Stambaugh et al. | |
| 6,004,316 A | 12/1999 | Laufer | |
| 6,063,085 A | 5/2000 | Tay et al. | |
| 6,077,261 A | 6/2000 | Behl et al. | |
| 6,629,534 B1 | 10/2003 | St. Goar et al. | |
| 6,752,813 B2 | 6/2004 | Goldfarb et al. | |
| 6,939,348 B2 * | 9/2005 | Malecki et al. | 606/41 |
| 7,165,552 B2 | 1/2007 | Deem et al. | |
| 7,186,251 B2 | 3/2007 | Malecki et al. | |
| 7,226,467 B2 | 6/2007 | Lucatero et al. | |
| 7,257,450 B2 | 8/2007 | Auth et al. | |
| 7,293,562 B2 | 11/2007 | Malecki et al. | |
| 7,311,701 B2 | 12/2007 | Gifford et al. | |
| 2004/0003819 A1 | 1/2004 | St. Goar et al. | |

(Continued)

FOREIGN PATENT DOCUMENTS

WO    WO 2007/100067 A1    9/2007

(Continued)

*Primary Examiner* — Michael Peffley
*Assistant Examiner* — Daniel Fowler
(74) *Attorney, Agent, or Firm* — Buchanan Ingersoll & Rooney PC

(57) ABSTRACT

A PFO closing device includes a suction and hold portion at a distal portion of a catheter for sucking and holding biological tissue of a foramen ovale valve and an atrial septum secundum from one side, an electrode portion on the side contacting the biological tissue; a negative pressure supply unit for applying negative pressure to the suctional portion and hold portion, a hold mechanism adapted to protrude from the distal tip of the catheter, and be inserted into the foramen ovale to hold the foramen ovale valve while pressing it from the other side and an energy supply unit for supplying energy to the electrode portion. Energy is supplied from the energy supply unit to the electrode portion, and the foramen ovale valve and the atrial septum secundum are mutually fused together.

13 Claims, 12 Drawing Sheets

U.S. PATENT DOCUMENTS

| | | |
|---|---|---|
| 2004/0030382 A1 | 2/2004 | St. Goar et al. |
| 2004/0039442 A1 | 2/2004 | St. Goar et al. |
| 2004/0044350 A1 | 3/2004 | Martin et al. |
| 2004/0049207 A1 | 3/2004 | Goldfarb et al. |
| 2004/0092962 A1 | 5/2004 | Thornton et al. |
| 2004/0225300 A1 | 11/2004 | Goldfarb et al. |
| 2004/0230185 A1* | 11/2004 | Malecki et al. .................. 606/2 |
| 2004/0243122 A1 | 12/2004 | Auth et al. |
| 2004/0267191 A1 | 12/2004 | Gifford, III et al. |
| 2005/0021056 A1 | 1/2005 | St. Goar et al. |
| 2005/0021057 A1 | 1/2005 | St. Goar et al. |
| 2005/0033288 A1 | 2/2005 | Auth et al. |
| 2005/0033446 A1 | 2/2005 | Deem et al. |
| 2005/0080406 A1 | 4/2005 | Malecki et al. |
| 2005/0131401 A1 | 6/2005 | Malecki et al. |
| 2005/0131460 A1 | 6/2005 | Gifford, III et al. |
| 2005/0192626 A1 | 9/2005 | Widomski et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2006/0020275 A1 | 1/2006 | Goldfarb et al. |
| 2006/0027241 A1 | 2/2006 | Malecki et al. |
| 2006/0074410 A1 | 4/2006 | Malecki et al. |
| 2006/0241581 A1 | 10/2006 | Malecki et al. |
| 2006/0241582 A1 | 10/2006 | Malecki et al. |
| 2006/0241583 A1 | 10/2006 | Malecki et al. |
| 2006/0241584 A1 | 10/2006 | Malecki et al. |
| 2006/0247612 A1 | 11/2006 | Malecki et al. |
| 2006/0271030 A1* | 11/2006 | Francis et al. ................. 606/27 |
| 2006/0271040 A1 | 11/2006 | Horne et al. |
| 2006/0271089 A1 | 11/2006 | Alejandro et al. |
| 2006/0276779 A1 | 12/2006 | Malecki et al. |
| 2006/0276846 A1 | 12/2006 | Malecki et al. |
| 2007/0010806 A1 | 1/2007 | Malecki et al. |
| 2007/0027445 A1 | 2/2007 | Gifford et al. |
| 2007/0038293 A1 | 2/2007 | St.Goar et al. |
| 2007/0044811 A1 | 3/2007 | Deem et al. |
| 2007/0078485 A1 | 4/2007 | Deem et al. |
| 2007/0088355 A9 | 4/2007 | Auth et al. |
| 2007/0093804 A1 | 4/2007 | Kaveckis et al. |
| 2007/0093805 A1 | 4/2007 | Auth et al. |
| 2007/0100324 A1 | 5/2007 | Tempel et al. |
| 2007/0100356 A1 | 5/2007 | Lucatero et al. |
| 2007/0106214 A1 | 5/2007 | Gray et al. |
| 2007/0112347 A1 | 5/2007 | Malecki et al. |
| 2007/0118155 A1 | 5/2007 | Goldfarb et al. |
| 2007/0123824 A1 | 5/2007 | Kaveckis |
| 2007/0123851 A1 | 5/2007 | Alejandro et al. |
| 2007/0123852 A1 | 5/2007 | Deem et al. |
| 2007/0129737 A1 | 6/2007 | Goldfarb et al. |
| 2007/0203479 A1 | 8/2007 | Auth et al. |
| 2007/0287999 A1 | 12/2007 | Malecki et al. |
| 2007/0299434 A1 | 12/2007 | Malecki et al. |
| 2008/0004658 A1 | 1/2008 | Malecki et al. |
| 2008/0009859 A1 | 1/2008 | Auth et al. |
| 2008/0051703 A1 | 2/2008 | Thornton et al. |
| 2008/0051807 A1 | 2/2008 | St. Goar et al. |
| 2008/0058683 A1 | 3/2008 | Gifford et al. |
| 2008/0097489 A1 | 4/2008 | Goldfarb et al. |
| 2008/0140064 A1 | 6/2008 | Vegesna |
| 2008/0140068 A1 | 6/2008 | Taimisto |
| 2008/0140069 A1 | 6/2008 | Filloux et al. |
| 2008/0140070 A1 | 6/2008 | Filloux et al. |
| 2008/0140071 A1 | 6/2008 | Vegesna |
| 2008/0140074 A1 | 6/2008 | Horne et al. |
| 2008/0140112 A1 | 6/2008 | Horne |
| 2008/0140113 A1 | 6/2008 | Taimisto |
| 2008/0140170 A1 | 6/2008 | Filloux et al. |

FOREIGN PATENT DOCUMENTS

WO  WO 2008/073727 A1  6/2008

\* cited by examiner

[FIG1]
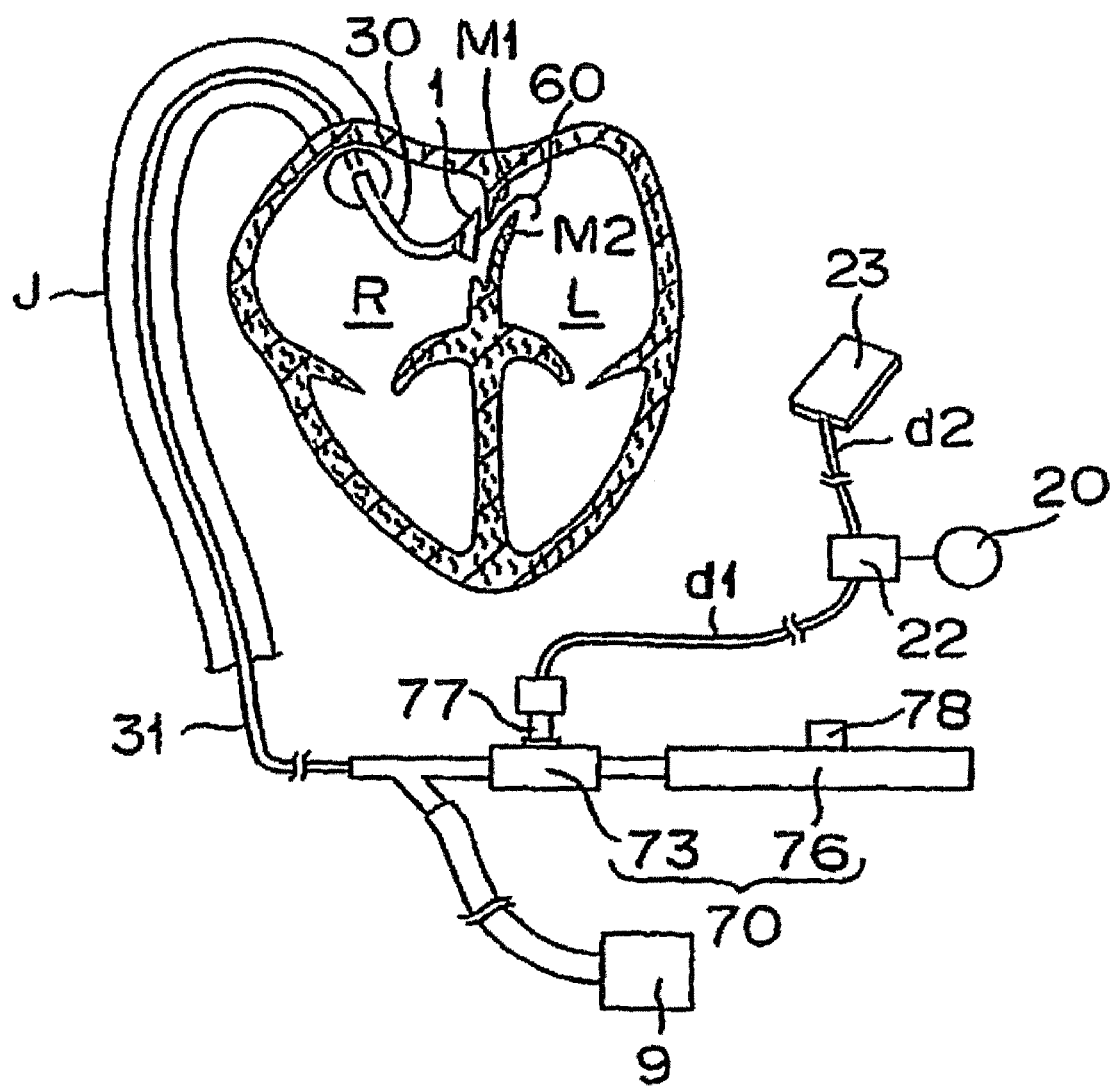

【FIG2】
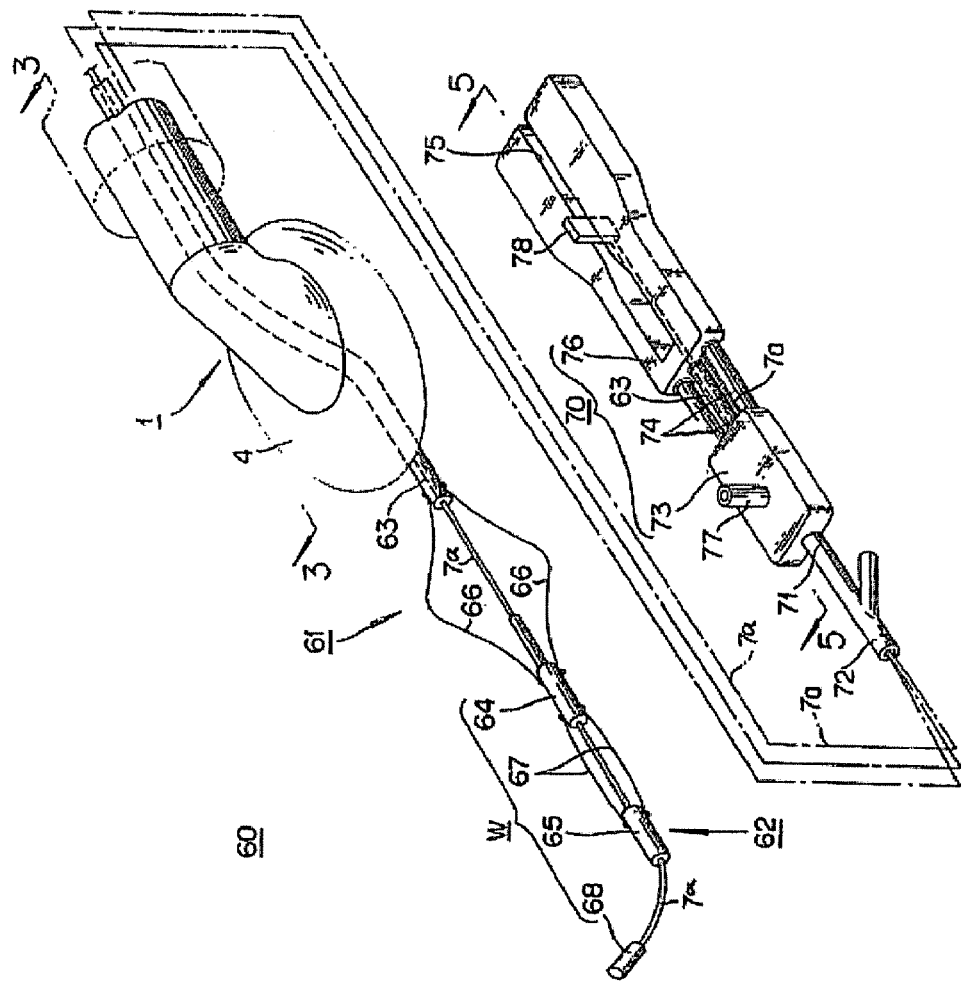
【FIG3】
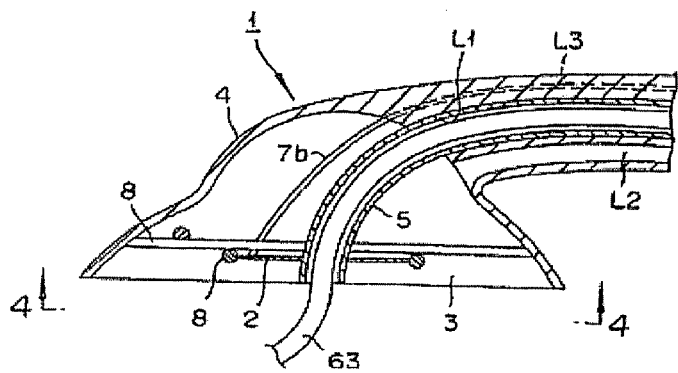

[FIG4]
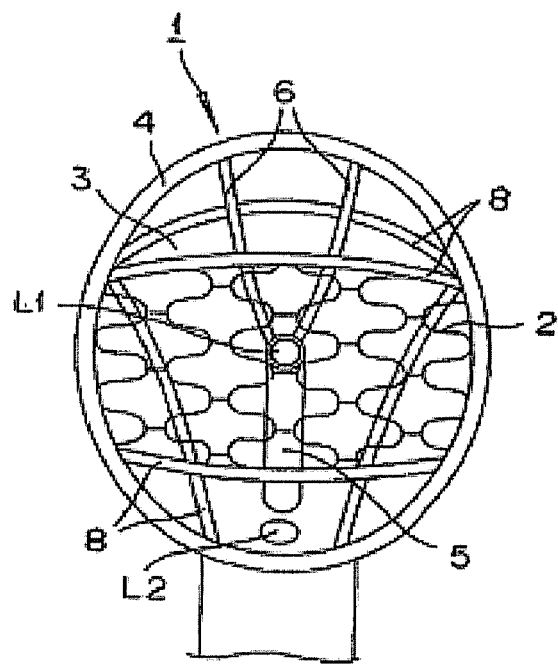
[FIG5]
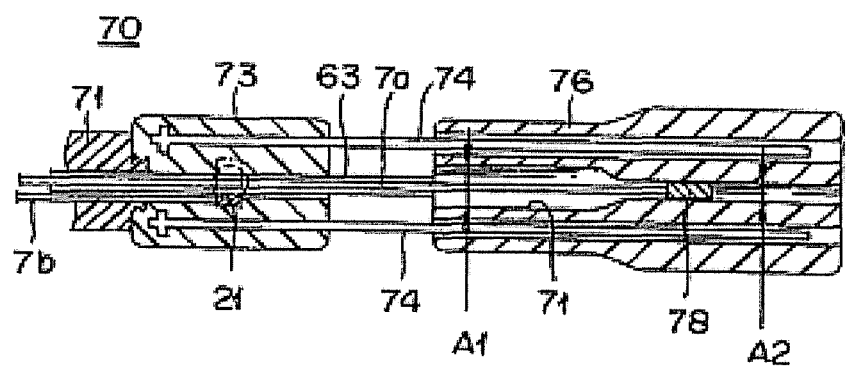

[FIG6]
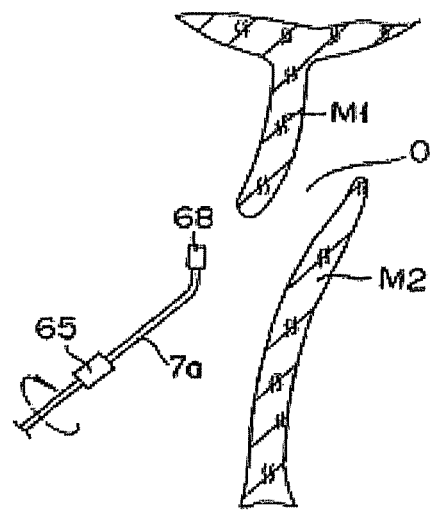
[FIG7]
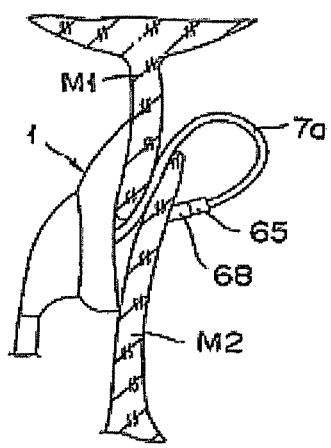

[FIG8]
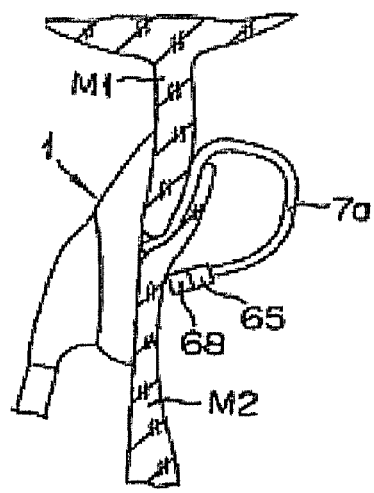
[FIG9]
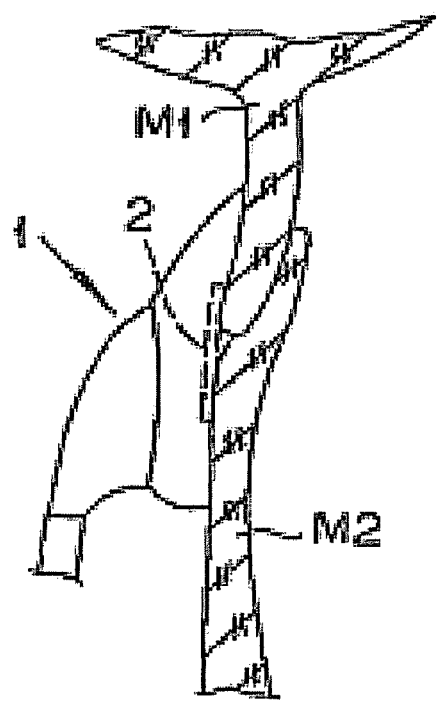

[FIG10]
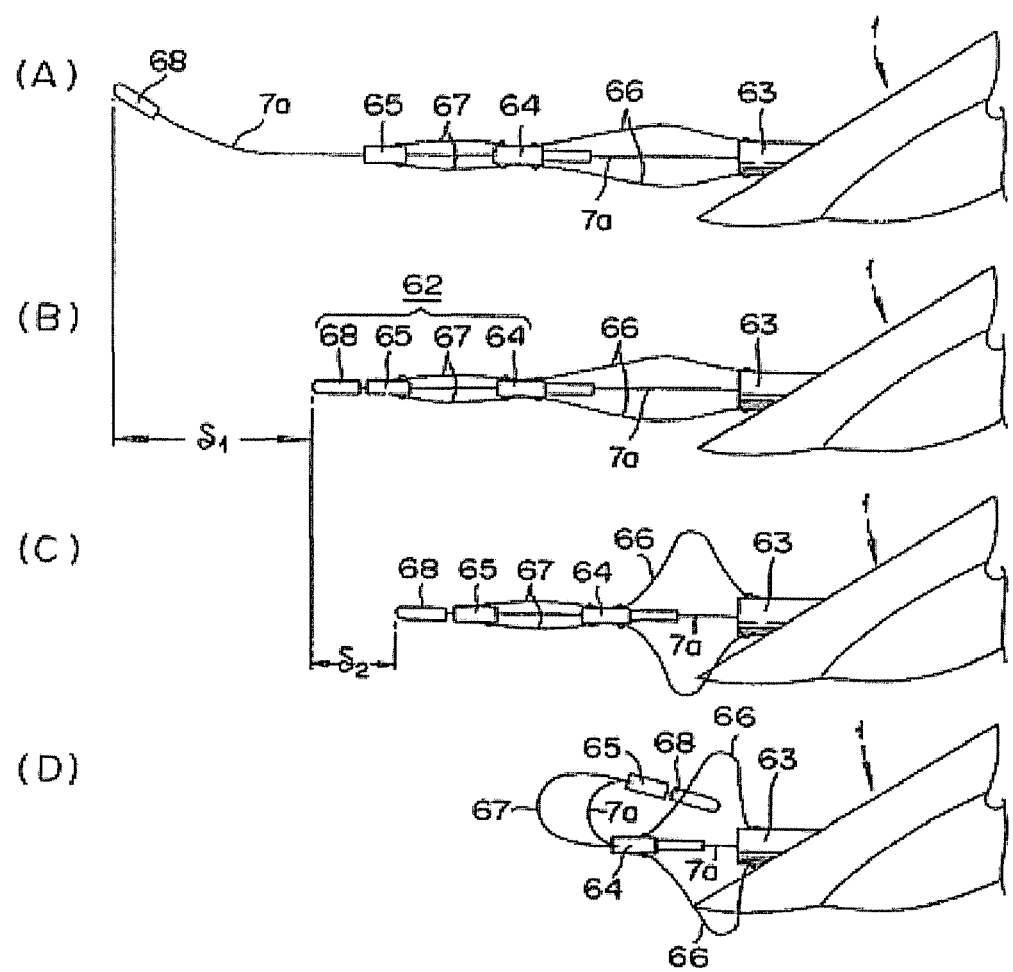

[FIG11]
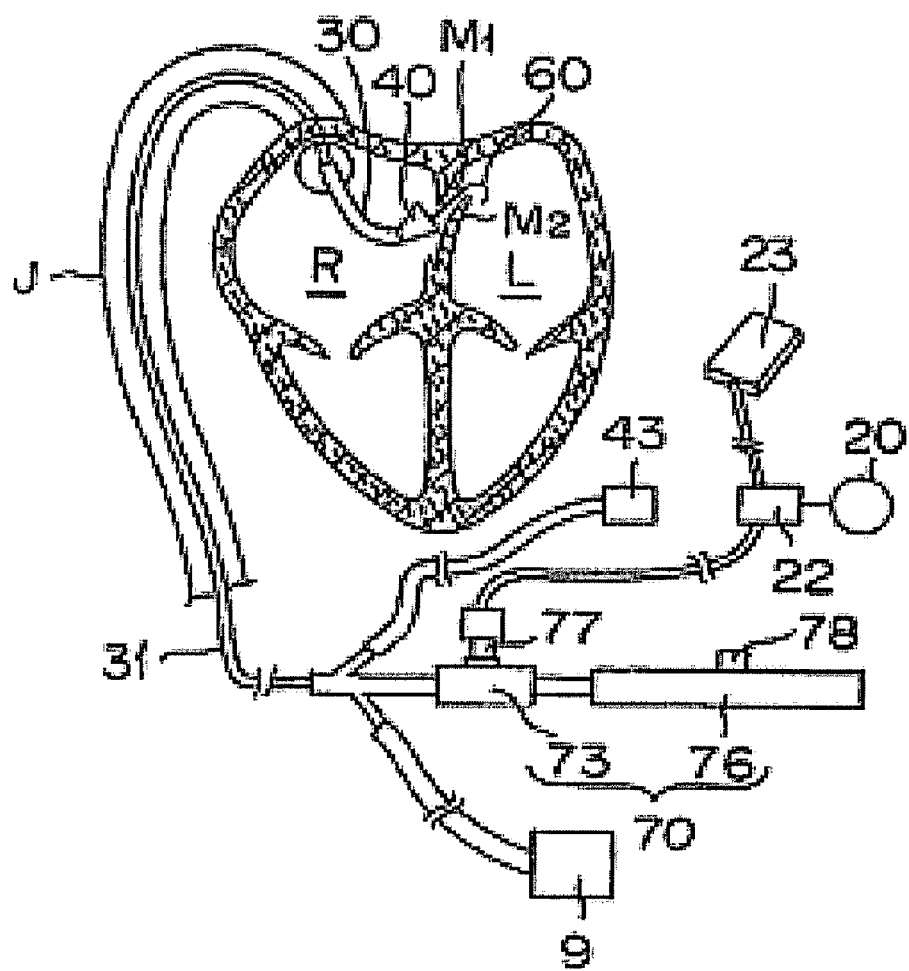

[FIG12]
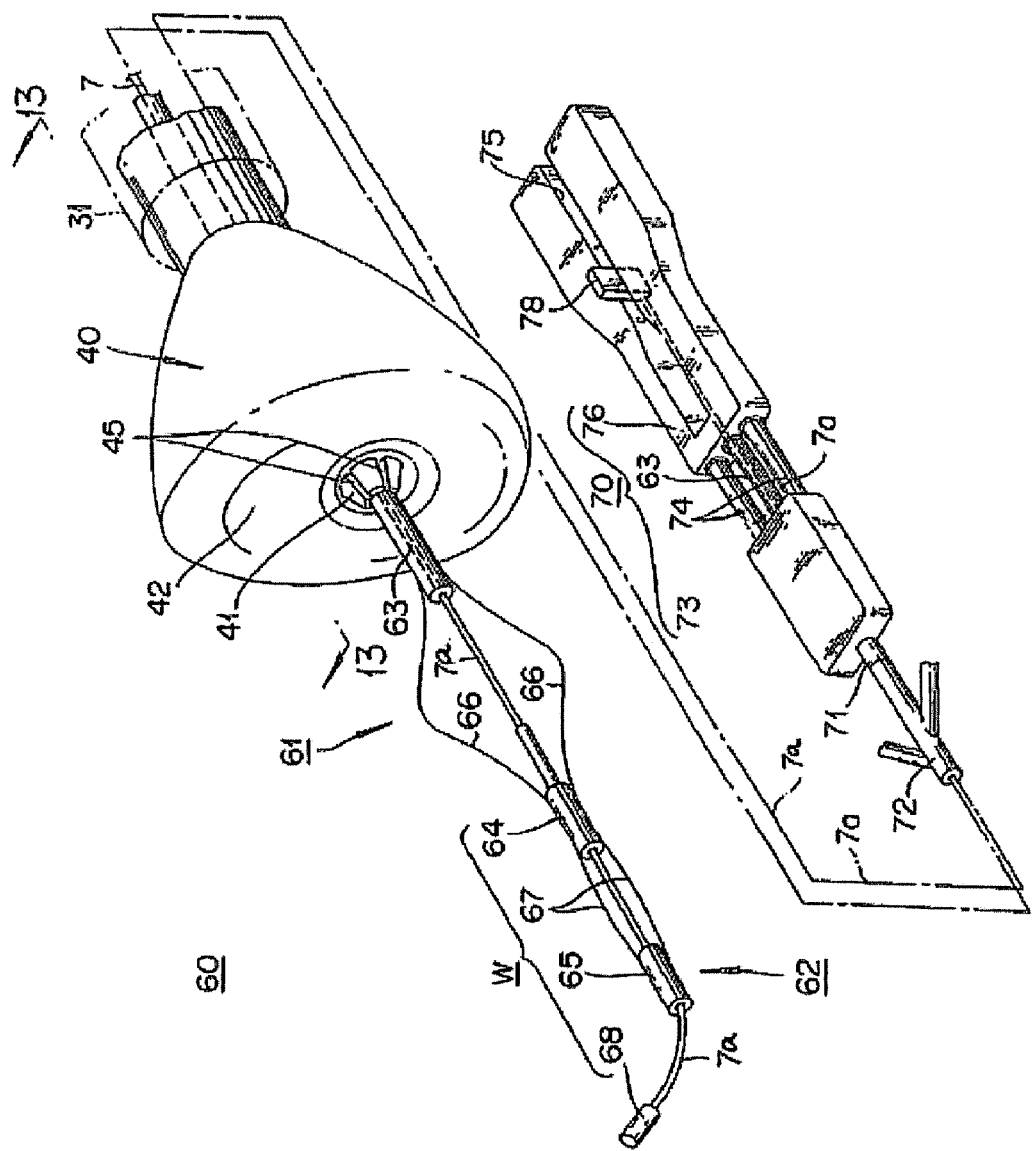

[FIG13]
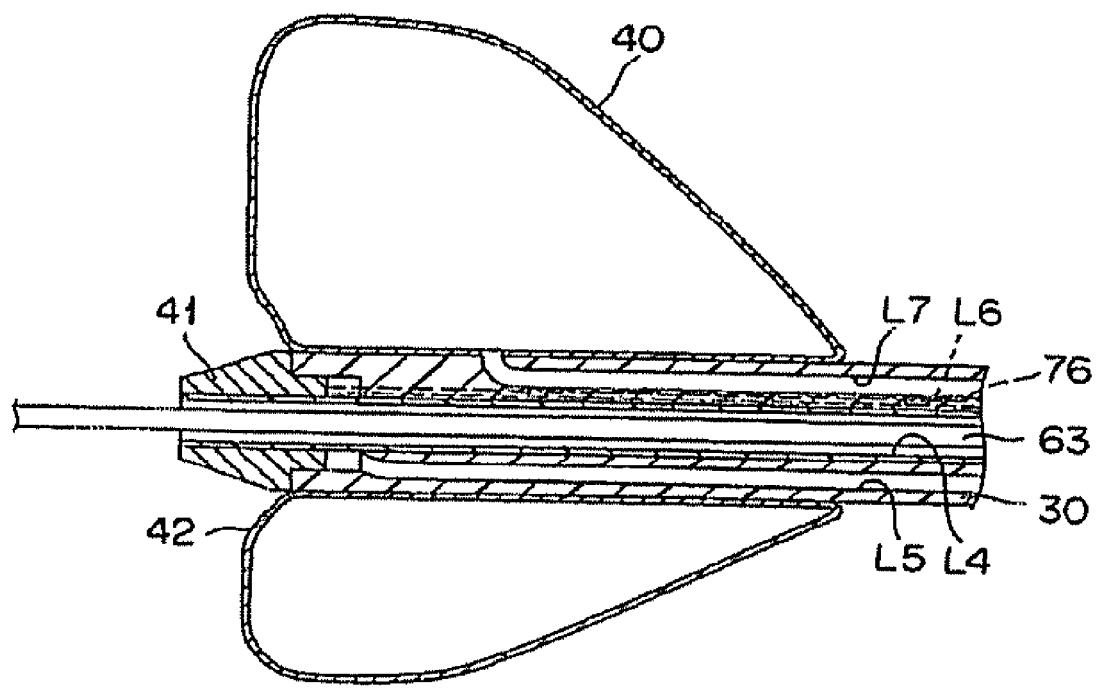

[FIG14]
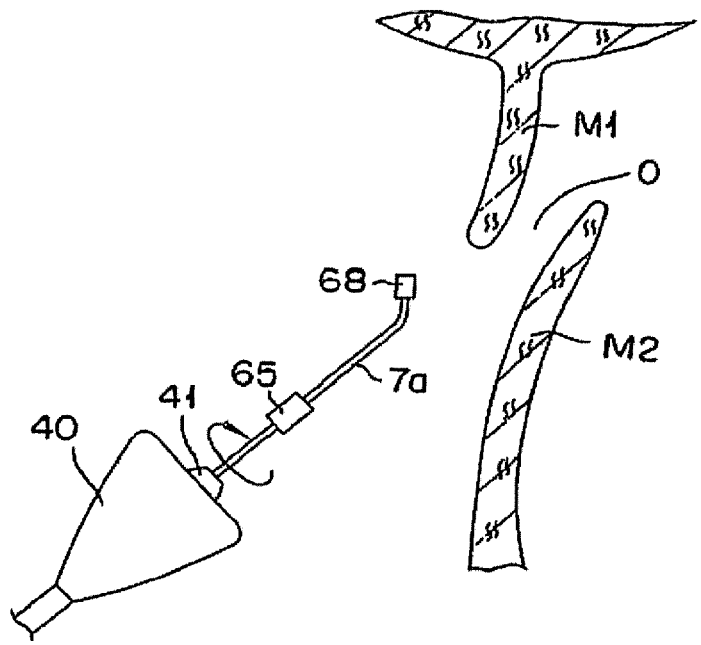
[FIG15]
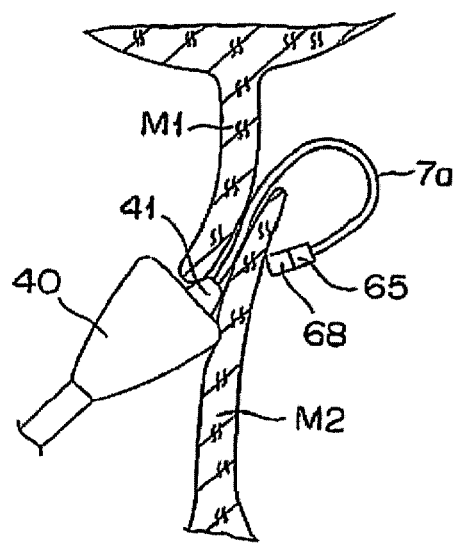

[FIG16]
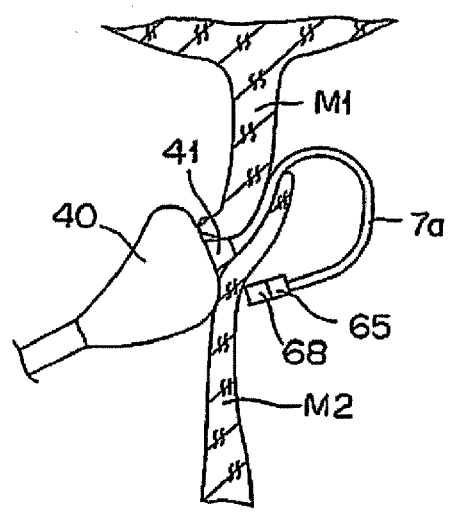
[FIG17]
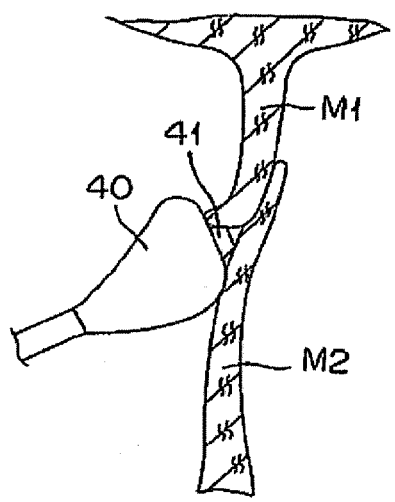

【FIG18】
(A)
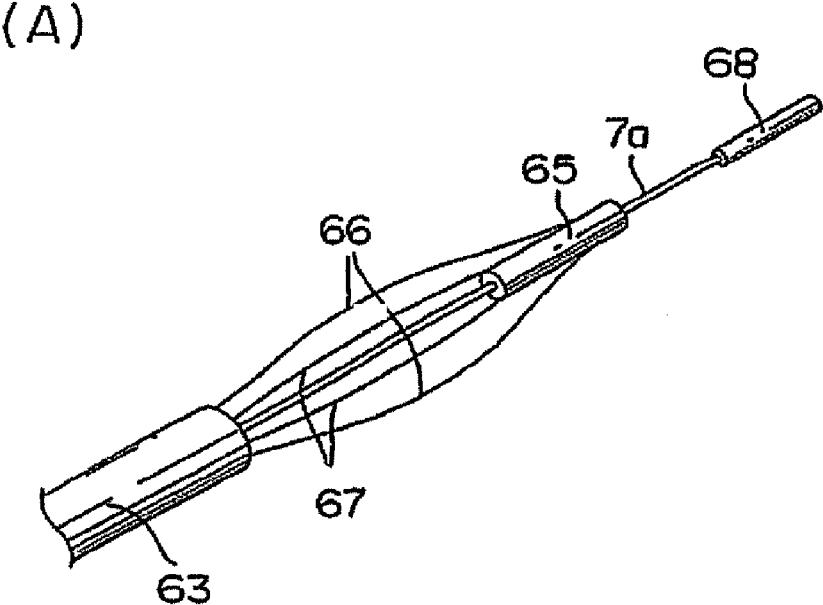
(B)
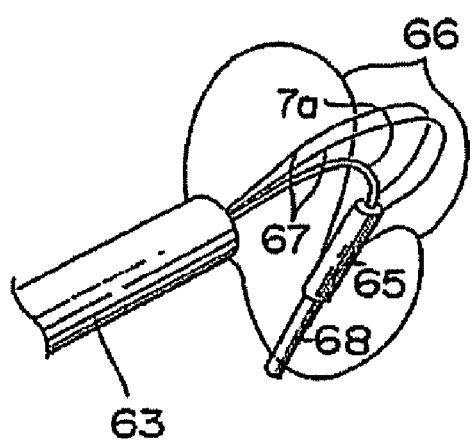

PFO CLOSING DEVICE

This application is based on and claims priority under 35 U.S.C. §119(e) with respect to U.S. Provisional Application No. 60/976,130 filed on Sep. 28, 2007, the entire content of which is incorporated herein by reference. This application is also based on and claims priority under 35 U.S.C. §119(a) with respect to Japanese Patent Application 2007-221905 filed Aug. 28, 2007, the entire content of which is hereby incorporated by reference.

TECHNICAL FIELD

The present invention generally relates to a medical device. More specifically, the invention pertains to a patent foramen ovale (PFO) closing device for closing a PFO in a person's heart.

BACKGROUND DISCUSSION

Recently, patent foramen ovale (hereinafter referred to as PFO) has been identified as a cardiac factor in strokes and migraines. The PFO is a symptom in which the oval foramen (foramen ovale) for shortcircuiting blood between the left and right sides in the heart in the fetal period of a person's life remains even after the person has gown up. It is said that 20-30% of grown-up people have this disease.

The foramen ovale occurs at a septum secundum (Septum Secundum, hereinafter, referred to as atrial septum secundum) of the heart. The pressure on the left atrium side normally exceeds the pressure on the right atrium side in the heart and so the foramen ovale is occluded by a septum primum (Septum Primum, hereinafter, referred to as foramen ovale valve). However, when the pressure on the right atrium side exceeds the pressure on the left atrium side on a strain occasion (for example, when coughing, when holding on) or the like, the foramen ovale valve opens to the left atrium side and blood can flow from the right atrium side (venous side) into the left atrium side (arterial side). When a thrombus is included in this blood, the thrombus is shifted from the venous side to the arterial side, flows in a route of left atrium→left ventricle→aorta→brain, and can become a factor for a stroke, migrane or the like.

Examples of the treatment of such a disease include pharmacotherapy (aspirin, warfarin, or the like), closure of the PFO by percutaneous catheterization, and open heart surgery by extracorporeal circulation. Pharmacotherapy is the treatment which should be selected first, but it can be difficult to manage the dosage, and bleeding may not cease easily during the dosage. Percutaneous catheterization and the open heart surgery are radical treatments and remove the fear of recurrence, though they are invasive procedures. At the present stage, of these closure procedures, open heart surgery is more assured. However, taking into account the risk attendant on the extracorporeal circulation and the magnitude of the invasion attendant on skin incision, the treatment by percutaneous catheterization is more desirable, if it produces the same effect as that of the open heart surgery.

Devices for closure by use of percutaneous catheterization can be used also in the cases of closing a defect, such as cogenital atrial septal defect (ASD), PFO, ventricular septal defect (VSD), patent ductus arteriosus (PDA), etc. The conventional devices, however, are based on clamping the SP and the SS by use of a disk-like membrane or anchor member for closing the defect, and they are left indwelling in the patient's body.

The membrane and the anchor member are foreign matters for the body, and thrombi are liable to deposit thereon. Particularly, when a thrombus deposits on the disk-like membrane on the side of the left atrium of the heart, it may flow downstream to cause stroke, or may break the SP which is small in wall thickness. In addition, these members may be positionally deviated, instead of being positionally fixed in the state of clamping the relevant tissues.

Consequently, recently, there has been proposed a PFO closing device which is described in Patent Document 1 (U.S. Application Publication No. 2006/0271030) and in Patent Document 2 (U.S. Application Publication No. 2007/0093804).

The PFO closing device described in Patent Document 1 of U>S>Application Publication No. 2006/0271030 is such that a suctionable suction portion is provided at a distal portion of a catheter thereof; a foramen ovale valve is sucked and pulled from the right atrium side by this suction portion and closed; and tissue is fused by applying energy by way of an electrode portion.

The PFO closing device described in Patent Document 2 of U.S. Application Publication No. 2007/0093804 is such that an expandable/shrinkible balloon is provided at a distal portion of the catheter thereof and at the same time, a suctionable suction portion is provided at the distal side of the balloon. While holding an atrial septum secundum by the balloon from the right atrium side, a foramen ovale valve is sucked and pulled by the suction portion and closed; and tissue is fused by applying energy by way of an electrode portion.

However, in either closing device of Patent Documents 1 and 2 mentioned above, there is a concern that the foramen ovale valve may not be sucked and blood is sucked excessively if the foramen ovale valve is distanced from the atrial septum secundum at the time of sucking. Also, in either closing device of the Patent Documents 1 and 2, the positioning of the electrode portion of the catheter is executed by a guide wire which is inserted into the foramen ovale, but the center of the suction portion or the electrode portion does not always coincide with the center of the foramen ovale, so that there is a problem that it is difficult to arrange the electrode portion at a desirable region for being applied with energy.

SUMMARY

According to one aspect, a patent foramen ovale closing device which fuses together a foramen ovale valve and an atrial septum secundum comprises a catheter, a suction and hold portion at the distal portion of the catheter engageable with biological tissue of the foramen ovale valve and the atrial septum secundum from one side to suck and hold the foramen ovale valve and the atrial septum secundum toward one another, an electrode, and a negative pressure supply unit connected to the suction and hold portion for applying negative pressure to the suction and hold portion. A contact member is connected to an elongated operation member movably positioned in the catheter to move the contact member distally beyond the suction and hold portion and into contact with the foramen ovale valve from an opposite side of the foramen ovale valve that is opposite the one side to apply an urging force urging the foramen ovale valve toward the atrial septum secundum, and an energy supply unit is connected to the electrode. The contact member is positionable on the other side of the foramen ovale valve and the atrial septum secundum to apply the urging force to the foramen ovale valve while the suction and hold portion is positionable on the one side of the foramen ovale valve and the atrial septum secundum so that operation of the negative pressure supply unit causes the foramen ovale valve and the atrial septum secundum to be sucked and held toward one another, and operation of the energy supply unit causes energy to be supplied to the electrode to fuse together the foramen ovale valve and the atrial septum secundum.

According to another aspect, a PFO closing device includes a suction and hold portion at a distal portion of a catheter for sucking and holding tissue of a foramen ovale valve and an atrial septum secundum from one side, an electrode portion on a side of the suction and hold portion which contacts the tissue of the foramen ovale valve and the atrial septum secundum, a negative pressure supply unit connected to the suction and hold portion for applying negative pressure to the suction and hold portion, a hold mechanism operable to protrude from a distal tip of the catheter through forward movement of the hold mechanism for insertion into the foramen ovale and to bend into a position to contact the foramen ovale valve from an other side opposite the one side and press the foramen ovale valve toward the atrial septum secundum, and an energy supply unit connected to the electrode portion for supplying energy to the electrode portion. The foramen ovale valve and the atrial septum secundum are sucked and held by the suction and hold portion in a state in which the foramen ovale valve is pressed by the hold mechanism toward the atrial septum secundum as energy is supplied from the energy supply unit to the electrode portion to fuse together the foramen ovale valve and the atrial septum secundum.

The hold mechanism is adapted to be inserted into the foramen ovale and holds the foramen ovale valve from the other side while pressing it, so that in a state in which the foramen ovale valve and the atrial septum secundum approach one another by the hold mechanism, it is possible to suck them together by the suction and hold portion and it is possible to pull the foramen ovale valve and to attach/contact it closely with the atrial septum secundum. Consequently, for example, even in a case in which the space between the atrial septum secundum and the foramen ovale valve is large, it is possible to fuse the atrial septum secundum and the foramen ovale valve by closely attaching them. Also, the space between the atrial septum secundum and the foramen ovale valve becomes small, so that it is possible to repress a phenomenon that blood is sucked excessively from the suction and hold portion.

An elongated operation member provided at the catheter is movable forward and backward, and can be moved to protrude beyond the distal tip of the catheter. It is thus possible to operate the hold mechanism by operating the operation member forward and backward in the axial direction, improving the safety and ease of the procedure, while making it possible to execute the procedure safely, accurately and also speedily.

The hold mechanism with the operation member can be rotatable in the catheter, centering around the axis, and so even if the foramen ovale is deformed variously, it is possible to insert the distal tip of the device into the foramen ovale regardless of the shape of the foramen ovale valve, thus improving possible not only to simplify the procedure but also to execute it speedily.

The hold mechanism can include a positioning hold mechanism for positioning the suction and hold portion and the electrode portion at predetermined positions with respect to the foramen ovale, and so it is possible to position the suction and hold portion at a suitable position At the time of sucking, it is possible to pull the foramen ovale valve efficiently, to position the electrode portion at a suitable position and to fuse the suitable position.

The positioning hold mechanism can be operable to move an elongated operation member back and forth to protrude distally beyond the catheter tip, to displace an elastic member outward by the operation of the operation member in the axial direction, and position the suction and hold portion and the electrode portion at the center portion of the foramen ovale by the elastic engagement of the elastic member with respect to the inner edge of the foramen ovale. The elastic member presses the inner edge of the foramen ovale with approximately equal elastic force, so that it is possible to center-align the suction and hold portion and the electrode portion with respect to the foramen ovale.

With the hold mechanism including a bending mechanism for bending the distal portion of the operation member by moving the elongated operation member to protrude from the distal tip of the catheter, it is possible to arrange the distal portion of the operation member to face the suction and hold portion and to hold the foramen ovale valve from the other side by inserting the hold mechanism into the foramen ovale and by bending the bending mechanism.

The bending mechanism can include a main tube positioned in the catheter and operational from the outside, with an operation member provided in the main tube so as to move forward and backward freely in the axial direction and to protrude from the distal tip of the main tube. In addition, the bending mechanism can include a middle sleeve body and a distal tip sleeve body provided coaxially with the operation member, and distal tip sleeve body and the middle sleeve body are coupled by an elastic wire;

In addition, a contact member which can be attached to the distal tip sleeve body. The distal tip sleeve body and the bump member can be engaged with one another by operation of the operation member to bend the elastic wire and at the same time displace the foramen ovale valve so as to be held, to facilitate positioning and holding of the foramen ovale valve more certainly, with improved safety, convenience, accuracy and speediness of the procedure.

The energy supply unit can be a monopolar system in which energization is executed between the electrode portion and a counterpart pole plate provided on the outside of the body. It is thus possible to heat and fuse the foramen ovale valve and the atrial septum secundum which are positioned between the electrode portion and the counterpart pole plate.

The electrode portion can include an electrode contacting the foramen ovale valve and an electrode contacting the atrial septum secundum, and the energy supply unit can be a bipolar system in which energization is executed between the electrodes. It is possible to energize only the vicinity of the region to be fused to decrease the influence to a human body.

The suction and hold portion can be an expandable and shrinkable expansion portion provided at the distal portion of the catheter, wherein fluid flows in/out with respect to the proximal portion of the catheter.

The suction and hold portion can be constructed so that the suction and hold surface applied with negative pressure by the negative pressure supply unit is provided on the side of the expansion portion contacting with the biological tissue. In addition, the electrode portion can be provided on the suction and hold surface. The foramen ovale valve and the atrial septum secundum can be pulled closely together by the negative pressure generated on the suction and hold surface. It is possible to execute the fusion of the foramen ovale valve and the atrial septum secundum more certainly.

The suction and hold portion can be an expandable and shrinkible expansion portion which is provided at the distal portion of the catheter and flows fluid in/out with respect to the proximal portion of the catheter, the suction and hold surface applied with negative pressure by the negative pressure supply unit is provided on the side of the expansion portion contacting with the biological tissue and the electrode portion is provided on the suction and hold surface, it is possible to pull the foramen ovale valve and attach the foramen ovale valve and the atrial septum secundum closely by the negative pressure generated on the suction and hold surface, so that it is possible to execute the fusion of the foramen ovale valve and the atrial septum secundum more certainly.

The suction and hold portion can be formed with an opening portion applied with the negative pressure by the negative pressure supply unit on the side contacting the biological tissue. In such an arrangement, the electrode portion can be is provided at the opening portion, whereby the foramen ovale valve is pulled, and the foramen ovale valve and the atrial septum secundum are closely drawn towards one another or engaged with one another by the negative pressure generated in the opening portion.

The hold mechanism can pass through the electrode portion so that the electrode portion can be positioned in the vicinity of the foramen ovale into which the hold mechanism is inserted.

A method of closing a foramen ovale by joining together a foramen ovale valve and an atrial septum secundum comprises applying a pushing force to the foramen ovale valve from one side of the foramen ovale valve to push the foramen ovale valve toward the atrial septum secundum, applying a suction force to the foramen ovale valve from a side of the foramen ovale valve opposite the one side to urge the foramen ovale valve into contact with the atrial septum secundum, the pushing force applied being different from the suction force, and fusing together the foramen ovale valve and the atrial septum secundum to close the foramen ovale.

BRIEF DESCRIPTION OF THE DRAWINGS

FIG. 1 is a schematic cross-sectional view showing a use state of a PFO closing device disclosed here according to a first exemplified embodiment.

FIG. 2 is an enlarged perspective view of a main portion of the device.

FIG. 3 is a cross-sectional view of the device taken along the section line 3-3 line in FIG. 2.

FIG. 4 is a plan view taken along the section line 4-4 in FIG. 3.

FIG. 5 is a cross-sectional view of the device taken along the section line 5-5 in FIG. 2.

FIG. 6 is a cross-sectional schematic illustration of the insertion of an operation member into a foramen ovale.

FIG. 7 is a cross-sectional schematic illustration of a state in which a foramen ovale valve is held by a hold mechanism.

FIG. 8 is a cross-sectional schematic illustration of a state in which a foramen ovale valve and an atrial septum secundum are sucked and held by a suction and hold portion.

FIG. 9 is a cross-sectional schematic illustration of a state in which electric current is applied to a foramen ovale valve and an atrial septum secundum by an electrode portion.

FIG. 10A-FIG. 10D are schematic side views of operation states of a distal portion of the PFO closing device.

FIG. 11 is a schematic cross-sectional illustration of a use state of a PFO closing device according to a second exemplified embodiment disclosed here.

FIG. 12 is an enlarged perspective view of a main portion of the second embodiment of the device shown in FIG. 11.

FIG. 13 is a cross-sectional view taken along the section line 13-13 in FIG. 12.

FIG. 14 is a cross-sectional schematic illustration of inserting the operation member into the foramen ovale.

FIG. 15 is a cross-sectional schematic illustration of a state in which a foramen ovale valve is held by a hold mechanism.

FIG. 16 is a cross-sectional schematic illustration of a state in which a foramen ovale valve and an atrial septum secundum are sucked and held by a balloon.

FIG. 17 is a cross-sectional schematic illustration of a state in which electric current is applied to a foramen ovale valve and an atrial septum secundum by an electrode portion.

FIGS. 18(A) and (B) are perspective views of another example of a positioning hold mechanism, in which FIG. 18A shows a stte before deformation and FIG. 18B shows a stte after deformation.

DETAILED DESCRIPTION

Referring initially to FIGS. 1-5, a first embodiment of a PFO closing device disclosed here is discussed.

Generally speaking, this device, as shown in FIG. 1, includes a suction and hold portion 1 for sucking and holding a foramen ovale valve M2 and an atrial septum secundum M1; an electrode portion 2 for contacting a biological tissue M (general term referring to M1, M2) sucked and held by the suction and hold portion 1; and an energy supply unit 20 for supplying energy by which the foramen ovale valve M2 and the atrial septum secundum M1 which are sucked and held are welded and fused, wherein the suction and hold portion 1 is installed in a percutaneous catheter 30 from a distal tip thereof so as to be protrudable and backward-movable. That is, the suction and hold portion is movably positioned in the catheter and is capable of being moved forwardly to protrude distally beyond the distal end of the catheter and rearwardly from such protruded position.

This device, when being used, is first inserted, for example, from a femoral vein J in a state in which there is housed, in a guiding catheter 31, the entire suction and hold portion 1 which is provided at the distal tip of the catheter 30. If the distal tip reaches the region of the heart at which the procedure is executed, the suction and hold portion 1 is moved in the distal direction to protrude from the distal tip of the guiding catheter 31 and sucks and holds the tissues of the atrial septum secundum M1 and the foramen ovale valve M2 of the heart having a defect O of the foramen ovale (hereinafter sometimes referred to as foramen ovale O) following a contact member 68 connected to an elongated operation member 7a applying an urging force to the foramen ovale valve M2 from the side opposite the suction and hold portion 1. In this suction and hold state, the electrode portion 2 is supplied with electric energy, both the tissues are welded and fused and the defect O is closed. It should be noted in the drawing that L denotes a left atrium and R denotes a right atrium.

In more detail, this PFO closing device, as shown in FIGS. 1 and 2, includes an operation unit 70 provided on the proximal side; a guiding catheter 31 mounted on the operation unit 70 for the proximal tip thereof; a catheter 30 provided in the guiding catheter 31, and the suction and hold portion 1 provided at a distal portion of the catheter 30. It should be noted in the following explanation that the side of the operation unit of the device is referred to as the proximal side, and the side of the suction and hold portion 1 or the foramen ovale valve M2 is referred to as the distal side.

The suction and hold portion 1 of the present exemplified embodiment, as shown in FIGS. 2-4, includes a housing 4 formed with an opening portion 3 to which negative pressure is applied for suction. With respect to the housing 4, the proximal portion of the housing 4 is provided at the distal tip of the catheter 30, and the housing is provided with a plurality of lumens L1 to L3 which communicate with the catheter 30.

A tube 5 is provided in the center of the opening portion 3 of the housing 4. The tube 5 extends from the lumen L1 and is fixed by a fixing portion 6 extended from the inside surface of the housing 4. Also, the opening portion 3 is provided with a plurality of reinforcement beams 8 so that the housing 4 can maintain its shape when negative pressure is applied to the inside of the housing 4. It is also possible to provide a reinforcement member such as a beam, a plate and the like on the outside of the housing 4.

The center of the opening portion of the housing 4 is provided with an electrode portion 2 surrounding the tube 5. The electrode portion 2 is formed, for example, by a wire configured in a wave shape. More specifically, the electrode portion can be comprised of a plurality of wavy-shaped wires as shown in FIG. 4. The suction can be executed also from the aperture of the electrode portion 2 (i.e., the opening or clearance between the adjacent wires), and it is possible for the electrode portion 2 to contact the biological tissue M over a relatively wide region. Also, by forming the electrode portion 2 to be a wire(s), it is relatively easy for the housing 4 to be elastically-deformed and to be housed in the guiding catheter 31. The shape of the electrode portion 2 is not limited by the shape mentioned above and it is also possible to employ a wire in a straight line shape or in a surface shape. The material forming the electrode portion 2 may be a SUS material, but it is preferable to use a material which does not exert bad influence to a living body such as, for example, gold, silver, platinum, tungsten, palladium or alloys of these, Ni—Ti alloy, titanium alloy and the like.

Also, the closing device here includes a positioning hold mechanism 60 (described in detail later) provided with a main tube 63 positioned in the lumen L1 of the catheter 30 and an operation member 7a. Before using the suction and hold portion 1, the suction and hold portion 1 and the electrode portion 2 are positioning-held by using the positioning hold mechanism 60 and in this case, the suction is executed by the suction and hold portion 1 in a state in which the operation member 7a is inserted into the foramen ovale O beforehand. In other words, the suction and hold portion 1 is configured so as to contact with the foramen ovale valve portion by passing through a passway which is restricted a certain degree by the operation member 7a.

The lumen L2 is provided in order to apply negative pressure to the inside of the housing 4 and communicates with a negative pressure supply unit 9 on the proximal side of the catheter 30.

A conductive wire 7b connected to the electrode portion 2 is positioned in the lumen L3 and this conductive wire 7b is connected to an energy supply unit 20 through an electrically-conductive member 21, a conductive wire d1 and a control unit 22 which will be mentioned later. Also, a counterpart pole plate 23 which forms a counterpart member with respect to the electrode portion 2 is connected to the energy supply unit 20 through a conductive wire d2. The counterpart member forms a return electrode for the electrode portion 2 in a monopolar system.

The suction and hold portion 1 in the illustrated embodiment is a separate member from the catheter 30, but it is also possible for the catheter 30 and the suction and hold portion 1 to be an integral one-piece structure. For a material constituting the suction and hold portion 1, it is possible to use a deformable elastic material, such as, for example, polyimide resin, polyurethane, PET, nylon, fluorine resin, polypropylene, silicon and the like.

The energy supply unit 20 is a unit for supplying electric energy to the electrode portion 2 and a well-known system construction is employed, so that a detailed description is avoided. If easiness of control is taken into account, it is preferable to employ an electrical power supply regardless of a direct-current power supply or an alternate-current power supply. However, it is also possible to employ not only this kind but also any kind of supply unit if it can supply energy in which the foramen ovale valve M2 and the atrial septum secundum M1 which are sucked and held by the suction and hold portion 1 are melted or fused by the heat and are pressed and fixed by an adhesive agent such as collagen, erastin and the like. For example, it is also possible to use a super sonic wave, laser, microwave or high frequency and the like.

Also, for an electric energy supply system, there is applied a monopolar system in which energization is carried out between the electrode portion 2 of the right atrium R side and the counterpart pole plate 23 provided at a backbone portion, but if a construction is employed in which two electrode portions becoming counterparts for the electrode contacted with the foramen ovale valve M2 and for the electrode contacted with the atrial septum secundum M1 are provided on the right atrium R side, it is also possible to apply a bipolar system in which energization is carried out between those two electrodes or the like. More specifically, it is possible to configure a bipolar system by arranging the electrode contacting the foramen ovale valve M2 and the electrode contacting the atrial septum secundum M1 at the opening portion 3 of the suction and hold portion 1 and by carrying out energization between these electrodes from the energy supply unit 20. It should be noted that if two pieces become necessary for the electrode, other lumens can be provided for connecting the energy supply unit 20 and the electrode in the housing 4 and in the catheter 30. Alternatively, if both the conductive wires connected with the two electrodes are coated by electrical insulation films and are insulated mutually, it is also possible to arrange them in the same lumen. According to the bipolar system, it is possible to energize only the vicinity of the region to be fused, so that it is possible to decrease influence to a human body. Also, it is possible to control electric current by the impedance between the electrodes, so that it is possible to have correspondence easily in response to the state of the tissues of the foramen ovale valve M2 and the atrial septum secundum M1 which differ depending on a person, and safety can be obtained.

The positioning hold mechanism 60, as shown in FIG. 2, generally, includes a positioning portion 61 (positioning mechanism) for positioning the suction and hold portion 1 and the electrode portion 2 with respect to a foramen ovale O and a holding portion 62 (hold mechanism) for holding and pressing the foramen ovale valve M2 with respect to the atrial septum secundum M1 held by the suction and hold portion 1 so as to be engaged closely or approaching such engagement, and normally it is housed in the guiding catheter 31, but it is pushed out from the guiding catheter 31 by the operation member 7a and a main tube 63 when using it.

To describe it in more detail, the center lumen L1 is provided with a main tube 63 for reinforcing the catheter 30 and for pulling and withdrawing the positioning hold mechanism 60 in/from the catheter 30; and an operation member 7a which is provided so as to move forward and backward freely in the axial direction.

The distal portion of the main tube 63 is provided with the positioning portion 61 which is operated so as to radially outwardly expand or radially inwardly shrink by the operation of the operation member 7a and which is constituted by a pair of a first elastic wires 66 coupling the main tube 63 and a middle sleeve body 64. The distal portion of the main tube is also provided with the hold portion 62 which includes a contact or bump member 68 provided at the distal portion of the operation member 7a, a distal tip sleeve body 65 and a pair of a second elastic wires 67 coupling the middle sleeve body 64 and the distal tip sleeve body 65, and which holds the foramen ovale valve M2 by the contact member 68 and the distal tip sleeve body 65.

With respect to the positioning portion 61, the operation member 7a is protruded from the distal tip of the main tube 63, the first elastic members 66 are displaced outward and inward by the operation of moving the operation member 7a forward and backward in the axial direction, respective first elastic members 66 press an inner fringe of the foramen ovale O with approximately equal elastic forces, and the suction and hold portion 1 and the electrode portion 2 are center-aligned with respect to the foramen ovale O. In other words, the positioning portion exhibits a function for positioning the suction and hold portion 1 and the electrode portion 2 which are positioned between both the first elastic members at the center portion of the foramen ovale O.

The holding portion 62 includes a bending mechanism W for bending the distal portion of the operation member 7a by operating the operation member 7a in the axial direction so as to move forward and backward. The bending mechanism W bends the holding portion 62 so as to face the suction and hold portion 1 and exhibits a function for holding the foramen ovale valve M2. Here, the bending mechanism W is constituted by the middle sleeve body 64, the distal tip sleeve body 65, the second elastic wire 67 for coupling both the sleeve bodies 64, 65 and the contact member 68.

The proximal tip of each first elastic wire 66 is welded on the distal tip of the main tube 63, and the distal side of each elastic wire is welded on the middle sleeve body 64. On the other hand, the proximal tip of each second elastic wire 67 is welded on the distal tip of the middle sleeve body 64 and the distal side of each elastic wire 67 is welded on the distal tip of the sleeve body 65.

It is preferable, for a specific example of the first and second elastic wires 66, 67, to use a metallic wire such as stainless steel, nickel-titanium, super elastic alloy (for example, Ni—Ti alloy) and the like with an outer diameter of around 0.1 mm to 0.5 mm. It is also possible to prevent the tissue from being wounded by coating a metallic wire with a (soft) resin tube.

The holding portion 62 has a construction in which the first elastic wire 66 of the proximal side bends prior to the second elastic wire 67 of the distal side; the positioning of the stick portion 2 is executed; subsequently, the operation member 7a itself is deformed accompanied by the contact member 68 and the distal tip sleeve body 65; and the positioning portion 61 holds the foramen ovale valve M2 after positioning the stick portion 2.

It is also possible, for example, to use the second elastic wire 67 having a higher material stiffness than that of the first elastic wire 66; and to form an easily-deformable portion by bending a portion of the first elastic wire 66 beforehand or the like and when a pulling force is applied, the first elastic wire 66 is bent previously (earlier than) compared with the second elastic wire 67 by the deformation of the easily-deformable portion.

In this manner, the first elastic wire 66 of the proximal side is engaged with an inner fringe of the foramen ovale O only by the movement or traction of the operation member 7a backward and the positioning of the stick portion 2 can be executed, and when applying further movement or traction, the second elastic wire 67 of the distal side protrudes and is deformed like an arc shape outwardly in the radial direction and it is possible to closely engage the foramen ovale valve M2 to the atrial septum secundum M1 or to approach it more closely so as to suck and pull the foramen ovale valve M2 relatively easily by the suction and hold portion 1.

Also, the operation member 7a is configured to be 360° rotatable centering around the axial line in the main tube 36 (axis of the main tube 36). With the operation member 7a being 360° rotatable, when the distal tip of the operation member 7a is inserted up to the vicinity of the foramen ovale O, it is possible to position-change the operation member 7a rotatingly and even if a state of the foramen ovale O is deformed variously, it is possible, regardless of the shape state thereof, to insert the distal tip of the device into the foramen ovale O. It is thus possible not only to simplify the procedure but also to execute it comparatively speedily.

The operation unit 70 is a preferably hand operated unit operable by the doctor or other user from the proximal end. As shown in FIG. 2 and FIG. 5, the operation unit 70 generally includes a first operation body 73 with which the proximal tip of the catheter 30 is coupled through a coupling member 71 and a Y connector 72, and a second operation body 76 approachable and separable with respect to the first operation body 73 by sliding along slide rails 74. Slide grooves are provided in the second operation body 76. The slide grooves are through-holes (through-slots) into which the pair of slide rails 74 protruding from the rear end side of the first operation body 73 are positioned. It should be noted in FIG. 2 that the operation unit 70 is illustrated in a demagnified manner because of space limitations.

The main tube 63 is positioned in the first operation body 73 and the rear end of the main tube 63 is coupled to the distal tip of the second operation body 76. Consequently, when applying backward movement or traction on the second operation body 76, it is possible to withdraw the whole positioning hold mechanism 60 within the center lumen L5 of the catheter 30. Possible materials constituting this main tube 63 include a deformable elastic material such as, for example, polyimide resin, polyurethane, PET, nylon, fluorine resin, polypropylene and the like. In addition, it is also possible to make the operation unit at hand 70 as a metallic pipe and to couple it with the main tube 63 of an elastic material.

With respect to the operation member 7a, the proximal tip thereof is mounted on a knob 78 which slides reciprocatingly in a slide groove 75 formed in the center of the second operation body 76. When sliding the knob 78 reciprocatingly in the slide groove 75, the whole operation member 7a moves reciprocatingly in the main tube 63.

The slide groove 75 is formed, as shown in FIG. 5, to be broader for the width A1 of the front half portion than the width A2 of the rear half portion and thus, in a case in which the knob 78 is positioned at the front half of the slide groove 75, it is possible to move the knob 78 in a tilting manner in a direction perpendicular to an axial line of the slide groove 75. Thus, it is possible to rotate the operation member 7a in the catheter 30 centering around the axial line and to adjust the distal tip position rotatingly. Consequently, when the operation member 7a is operated by operating the knob 78 according to the operation unit 70, it is possible to adjust not only the position in the forward and backward direction but also the rotational position and the convenience of the procedure for the insertion to the left atrium is improved considerably.

The conductive wire 7b connected to the electrode portion 2 is positioned in the lumen L3 and connected with the energy supply unit 20 through the electrically-conductive member 21 in the first operation body 73, a coupler 77, the conductive wire d1 and the control unit 22.

Also, it is possible for the operation member 7a to be made of any kind of member that is a fine hollow cylindrical wire possessing suitable stiffness properties, but it is preferable to use a fine tube such as, for example, stainless, Ni—Ti, titanium and the like.

With respect to the guiding catheter 31 of the present exemplified embodiment, the distal tip of the catheter is bent gently in an arc shape in order to make it easy to be inserted into the foramen ovale O between the foramen ovale valve M2 and the atrial septum secundum M1. The foramen ovale valve M2 and the atrial septum secundum M1 differ depending on the person, so that when the distal tip of the guiding catheter 31 is bent, the guiding catheter 31 itself is rotatingly moved and it is possible to insert the guiding catheter 31 into the foramen ovale O at a position in which the insertion becomes easier, and safety and convenience of the procedure are improved compared with the case of a straight shape.

The operation of the present exemplified embodiment is as follows.

FIG. 6 illustrates the situation in which an operation member is inserted into an foramen ovale, FIG. 7 shows a state in which the foramen ovale valve is held by the hold mechanism, FIG. 8 illustrates a state in which a foramen ovale valve and an atrial septum secundum are sucked and held by a suction and hold portion, FIG. 9 shows a state in which electric current is applied to a foramen ovale valve and an atrial septum secundum by the electrode portion, and FIGS. 10A-10D show various operational states of the PFO closing device.

In FIG. 10A to FIG. 10D, to help facilitate an understanding, shapes and positions of the second elastic wire 66 are shown by states in which the positions are shown by being displaced by 90° and those are different from the actual deformation states.

First, the surgery operator moves the second operation body 76 of the operation unit 70 backward with respect to the first operation body 73 to cause, for example, the elastically-deformed suction and hold portion 1 to be housed in (move into) the guiding catheter 31. In this state, the distal tip of the guiding catheter 31 is inserted from a predetermined position of the living body, using a guide wire as a guide, until it reaches the right atrium R. Here, it is also possible to insert only the guiding catheter 31 into the living body and afterward to insert the catheter 30 by making that guiding catheter 31 operate as a guide.

Next, the first operation body 73 is operated and the distal tip of the catheter 30 is moved forward to protrude into the left atrium L from the right atrium R through the foramen ovale O and thereafter, the knob 78 is moved forward. As shown in FIG. 10A and FIG. 6, the distal tip of the operation member 7a protrudes distally from the distal tip sleeve body 65 and is inserted into the left atrium L. It is possible to visually observe this protruding state from the outside if a marker is provided on the contact member 68 or the like, and it is possible to identify by touch the place in which the distal tip of the operation member 7a is positioned when by the distal tip of the operation member 7a contacts the inner wall of the left atrium L or the like by virtue of the protruding nature of the protrusion even in a case in which it is difficult to visually observe, so that the convenience is improved. It should be noted that the knob 78 is positioned at a wide front half portion of the slide groove 75 and when this is moved in a tilting manner, the sensitive or touch identification of the distal position becomes relatively easy.

After the identification of the distal position of the operation member 7a, the knob 78 is moved backward until, as shown in FIG. 10B, the contact member 68 of the operation member 7a contacts or engages the distal tip sleeve body 65 (amount of backward movement is [δ1] in FIG. 10B). Then, the first operation body 73 is operated, and the second elastic wire 67, and the suction and hold portion 1 are positioned in the vicinity of the foramen ovale valve M2 and the entire holding portion 62 is inserted into the left atrium L side.

When the knob 78 is further moved backward (amount of backward movement is [δ2] in FIG. 1C), the operation force of the backward movement is transmitted by the operation member 7a to the first elastic wire 66 firmly fixed on the distal tip of the main tube 63 through the contact member 68, the distal tip sleeve body 65, the second elastic wire 67 and the middle sleeve body 64, and the first elastic wire 66, as shown in FIG. 10C, protrudes and is deformed in an arc shape toward the outside in the radial direction. However, at this point in time, the second elastic wire 67 is not deformed.

Consequently, the first elastic wire 66 is deformed while pushing and widening the opening edge portion of the foramen ovale O, so that the electrode portion 2 and suction and hold portion 1 which are provided in close vicinity of the first elastic wire 66 is center-aligned with respect to the foramen ovale O and the electrode portion 2 and suction and hold portion 1 are positioned at the center of the foramen ovale O.

After the electrode portion 2 and the suction and hold portion 1 are positioned at the center of the foramen ovale O, the electrode portion 2 and the suction and hold portion 1 closely engage the atrial septum secundum M1 and the foramen ovale valve M2.

Thereafter, when the knob 78 is further operated to move backward to rearwardly move the middle sleeve body 64 until the rear end of the middle sleeve body 64 nearly engages the distal tip of the main tube 63, as shown in FIG. 10D, the first elastic wire 66 is not deformed so much anymore, but the second elastic wire 67 of the distal side protrudes and is deformed in an arc shape toward the outside in the radial direction by the operation force. Consequently, in the left atrium L, the contact member 68 and the distal tip sleeve body 65 curve and approach the suction and hold portion 1, so that the contact member 68 and the distal tip sleeve body 65 are pressed, as shown in FIG. 7, into engagement with the surface of the left atrium side of the foramen ovale valve M2 and holds the foramen ovale valve M2 by urging it towards (approaching) the atrial septum secundum M1.

In this state, the negative pressure supply unit 9 is operated and negative pressure is generated in the suction and hold portion 1, and the foramen ovale valve M2 is sucked and pulled. As a result, as shown in FIG. 8, the foramen ovale valve M2 is closely engaged or contacted with the atrial septum secundum M1. At that time, the foramen ovale valve M2 closely approaches the atrial septum secundum M1 side by the positioning hold mechanism 60, so that it is possible to pull the foramen ovale valve M2 efficiently. More specifically, for example in a case in which the aperture between the atrial septum secundum M1 and the foramen ovale valve M2 is relatively large, there is a possibility that only blood is sucked by the suction and hold portion 1 and the foramen ovale valve M2 is not pulled. However, here the foramen ovale valve M2 already closely approaches the atrial septum secundum M1 side (by virtue of the urging or pushing force applied by the contact member 68 and the distal tip sleeve body 65), so that it is possible to pull the foramen ovale valve M2 efficiently while also repressing the excessive suction of blood. In particular, there are inter-individual differences for the shapes of the atrial septum secundum M1 and the foramen ovale valve M2 and so there are various kinds (e.g., sizes and shapes) of aperture between the atrial septum secundum M1 and the foramen ovale valve M2 mentioned above. With the closing device disclosed here, it is possible to effectively operate taking into account variations in the aperture caused by the inter-individual differences. Also, the suction and hold portion 1 is positioned at the center of the foramen ovale O, so that it is possible to cover the foramen ovale O suitably by the suction and hold portion 1 and it is possible to execute the pulling of the foramen ovale valve M2 caused by the suction more effectively. The suction and hold portion 1 can be positioned, as shown in FIG. 7, such that the suction and hold portion (housing 4) extends across or spans both the atrial septum secundum M1 and the foramen ovale valve M2).

Next, while maintaining this suction state, the second operation body 76 is returned once and, as shown in FIG. 10B, the first elastic wire 66 and the second elastic wire 67 are straightened-out into a straight-line shape and thereafter, the second operation body 76 is operated to move backward and as shown in FIG. 9, the whole positioning hold mechanism 60 is withdrawn by the main tube 63 in the lumen L1 of the catheter 30.

Thereafter, while maintaining this suction state, the power supply unit 20A is controlled and when a predetermined electric current flows between the electrode portion 2 and the counterpart pole plate 23, the atrial septum secundum M1 and the foramen ovale valve M2 are heated by the supply of this electric energy. When the heating is continued while maintaining a fusion temperature, tissue of the atrial septum secundum M1 and tissue of the foramen ovale valve M2 melt and are mutually fused by an adhesive agent such as collagen, erastin and the like.

By controlling electric energy in the control unit 22, even if a portion of the electrode portion 2 is exposed in the blood, it is possible in this step to prevent the thrombus from being attached to the electrode portion 2. However, if coating for preventing thrombus attachment is applied on the surfaces of the electrode portion 2, the attachment of the thrombus is prevented more certainly and it is preferable.

When applying electric energy, the electrode portion 2 is positioned at the center of the foramen ovale O, so that it is possible to contact the electrode portion 2 to a suitable position and it is possible to execute the fusion efficiently.

When the tissues of the atrial septum secundum M1 and the foramen ovale valve M2 are fused, energization is stopped, the first operation body 75 is moved backward, the suction and hold portion 1 which exists at the distal tip of the catheter 30 is housed together with the positioning hold mechanism 60 in the guiding catheter 31 (i.e., the suction and hold portion 1 along with the positioning hold mechanism 60 are moved into the guiding catheter 31), and the guiding catheter 31 is pulled out from the living body.

According to the present exemplified embodiment, the atrial septum secundum M1 and the foramen ovale valve M2 are held by the suction, so that a sticking operation is not necessary and it is possible to decrease the occurrence of bad influence to a treatment portion.

FIGS. 11-13 illustrate a PFO closing device according to a second exemplified embodiment. Features of the closing device in this second embodiment that are the same as the first embodiment are identified with the same reference numerals in this embodiment, and a detailed description of such features is not repeated.

The PFO closing device according to the second exemplified embodiment includes an expandable and shrinkible expansion portion 40 for the suction and hold portion. The expansion portion 40 is, for example, a balloon 40, provided at the distal portion of the catheter 30, and the expansion/contraction thereof is made possible by flowing the fluid in/out from the proximal side of the catheter 30. It is preferable for the fluid which flows in/out from the balloon 40 to be physiological salt water and a contrast medium may be contained therein. The visibility under x-raying is improved by adding a contrast medium.

The closing device, as shown in FIG. 1, includes a balloon 40 (suction and hold portion) for sucking and holding a foramen ovale valve M2 and an atrial septum secundum M1; an electrode portion 41 for contacting a biological tissue M (general reference to M1, M2) sucked and held by the balloon 40; and a energy supply unit 20 for supplying energy by which the foramen ovale valve M2 and the atrial septum secundum M1, which are sucked and held, are welded or fused, wherein the balloon 40 in a shrunk state is installed in a percutaneous catheter 30 from a distal tip thereof so as to be movable forward to protrude from the distal end of the catheter and backward to be retracted from such protruding position.

This closing device, during use, is first inserted, for example, from a femoral vein J in a state in which there is housed in a guiding catheter 31 the balloon 40 in a shrunken (contracted) state, which is provided at the distal tip of the catheter 30. If the distal tip reaches the region of the heart at which the procedure is executed, the balloon 40 is expanded after protruding from the distal tip of the guiding catheter 31 and sucks and holds the tissues of the atrial septum secundum M1 and the foramen ovale valve M2 of the heart having a defect O of the foramen ovale (hereinafter referred to as foramen ovale O). In this suction and hold state, the electrode portion 41 is supplied with electric energy, both the tissues are welded and fused, and the defect O is closed.

In more detail, the balloon 40 of the present exemplified embodiment is formed, as shown in FIGS. 12 and 13, at the periphery centering around the catheter 30, a suction and hold surface 42 for contacting the biological tissue M is provided on the distal side of the balloon. It is also possible to provide a reinforcement member such as a beam, a plate and the like on the outside of the balloon 4.

In the catheter 30, there are formed lumens L4-L7 and the positioning hold mechanism 60 is positioned in the large lumen L4 at the center.

The lumen L5 is provided in order to apply negative pressure to the suction and hold surface 42 and communicates with a negative pressure supply unit 9 on the proximal side of the catheter 30.

A conductive wire 7b connected to the electrode portion 41 is inserted into the lumen L6 and this conductive wire 7b is connected to an energy supply unit 20 through an electrically-conductive member 21, a conductive wire d1 and a control unit 22. Also, a counterpart pole plate 23 which forms a counterpart member with respect to the electrode portion 41 is connected to the energy supply unit 20 through a conductive wire d2.

The lumen L7 communicates with the inside of the balloon 40 and communicates with a fluid supply unit 43 at the proximal portion. The fluid supply unit 43 controls expansion/contraction of the balloon 40 by allowing the flow of the fluid in/out with respect to the inside of the balloon 40 through the lumen L7.

The suction and hold surface 42 is provided with an electrode portion 41 which is positioned at the distal tip of the catheter 30. The electrode portion 41 has a conical shape in the illustrated embodiment. In addition, as shown in FIG. 12, the electrode portion 41 is provided with a plurality of axially extending slits 45 spaced apart from one another in the circumferential direction. These slits 45 pass through the lumen L5 and play a role to apply negative pressure to the suction and hold surface 42. Also, the center of the electrode portion 41 is provided with a through-hole communicating from the lumen L4 of the catheter 30, and the positioning hold mechanism 60 is inserted into this through-hole.

The shape of the electrode portion 41 is not limited to the shape mentioned above, and it is also possible to possess, for example, a wire shape similar to the first exemplified embodiment or a plate shape. The material forming the electrode portion 41 may be a SUS material, but it is preferable to use a material which does not exert bad influence to a living body such as, for example, gold, silver, platinum, tungsten, palladium or alloys of these, Ni—Ti alloy, titanium alloy and the like.

For the material constituting the balloon 40, it is possible to use a deformable elastic material, such as, for example, polyimide resin, polyurethane, PET, nylon, fluorine resin, polypropylene, silicon and the like.

For an electric energy supply system, there is applied a monopolar system in which energization is carried out between the electrode portion 41 of the right atrium R side and the counterpart pole plate 23 provided at a backbone portion. However, if a construction is employed in which two electrode portions becoming counterparts for the electrode contacted with the foramen ovale valve M2 and for the electrode contacted with the atrial septum secundum M1 are provided on the right atrium R side, it is also possible to apply a bipolar system in which energization is carried out between those two electrodes or the like. More specifically, it is possible to configure a bipolar system by arranging the electrode contacting the foramen ovale valve M2 and the electrode contacting the atrial septum secundum M1 at the suction and hold surface 42 of the balloon 40 and by carrying out energization between these electrodes from the energy supply unit 20. It should be noted that two pieces become necessary for the electrode becomes, so that there are provided another lumens for connecting the energy supply unit 20 and the electrode in the catheter 30. Alternatively, if both the conductive wires connected with the two electrodes are coated by electrical insulation films and are insulated mutually, it is also possible to arrange them in the same lumen. According to the bipolar system, it is possible to energize only the vicinity of the region to be fused, so that it is possible to decrease influence to other areas of the human body. Also, it is possible to control electric current by the impedance between the electrodes, so that it is possible to have correspondence relatively easily in response to the state of the tissues of the foramen ovale valve M2 and the atrial septum secundum M1 which differ depending on a person, and safety can be obtained.

The operation of the present exemplified embodiment is described below with reference to FIGS. 14-17.

FIG. 14 is a cross-sectional outlined view in which an operation member is inserted into a foramen ovale, FIG. 15 is a cross-sectional outlined view of a state in which a foramen ovale valve is held by a hold mechanism, FIG. 16 is a cross-sectional outlined view of a state in which a foramen ovale valve and an atrial septum secundum are sucked and held by a balloon and FIG. 17 is a cross-sectional outlined view of a state in which a foramen ovale valve and an atrial septum secundum are applied with electric current by the electrode portion.

First, the surgery operator moves the second operation body 76 of the operation unit 70 backward with respect to the first operation body 73 so that the contracted balloon 40 and the like are housed in the guiding catheter 31. In this state, the distal tip of the guiding catheter 31 is inserted from a predetermined position of the living body by using a guide wire as a guide until it reaches the right atrium R.

Next, the first operation body 73 is operated and the distal tip of the catheter 30 is moved to protrude to the left atrium L from the right atrium R through the foramen ovale O and thereafter, the knob 78 is moved forward and, as shown in FIG. 10A and FIG. 14, the distal tip of the operation member 7a protrudes from the distal tip sleeve body 65 and inserted into the left atrium L.

After identifying the distal position of the operation member 7a, as shown in FIG. 10B, the knob 78 is moved backward until the contact member 68 of the operation member 7a attaches to the distal tip sleeve body 65 (amount of backward movement is [δ1] n FIG. 10B). Then, the first operation body 73 is operated, and the second elastic wire 67, the balloon 40 are positioned in the vicinity of the foramen ovale valve M2 and the whole holding portion 62 is inserted into the left atrium L side.

When the knob 78 is further moved backward (amount of backward movement is [δ2] in FIG. 10C), this operation force for the backward movement is transmitted by the operation member 7a to the first elastic wire 66 firmly fixed on the distal tip of the main tube 63 through the contact member 68, the distal tip sleeve body 65, the second elastic wire 67 and the middle sleeve body 64, and the first elastic wire 66 is, as shown in FIG. 10C, protruded and deformed in an arc shape toward the outside in the radial direction. However, at this time point, the second elastic wire 67 is not deformed.

Consequently, the first elastic wire 66 is deformed while pushing and widening the opening edge portion of the foramen ovale O, so that the electrode portion 41 and the balloon 40 which are provided in close vicinity of the first elastic wire 66 is center-aligned with respect to the foramen ovale O, and the electrode portion 41 and the balloon 40 are positioned at the center of the foramen ovale O.

After the electrode portion 41 and the balloon 40 are positioned at the center of the foramen ovale O, the electrode portion 41 and the balloon 40 are attached to the atrial septum secundum M1 and the foramen ovale valve M2 closely.

Thereafter, further, the knob 78 is operated to move backward until a rear end of the middle sleeve body 64 engages or contacts the distal tip of the main tube 63, as shown in FIG. 10D. During this movement, the first elastic wire 66 is not further deformed so much, but the second elastic wire 67 of the distal side protrudes and is deformed in an arc shape toward the outside in the radial direction by the operation force. Consequently, in the left atrium L, the contact member 68 and the distal tip sleeve body 65 approach the balloon 40, so that the contact member 68 and the distal tip sleeve body 65 apply a pressing force, as shown in FIG. 15, by contacting or engaging the surface of the left atrium side of the foramen ovale valve M2 and hold the foramen ovale valve M2 by approaching the atrial septum secundum M1 (urging the foramen ovale valve M2 toward the atrial septum secundum M1).

In this state, the negative pressure supply source is operated and negative pressure is generated on the suction and hold surface 42 of the balloon 40. As shown in FIG. 16, the foramen ovale valve M2 is sucked and pulled, and is closely engaged with the atrial septum secundum M1. At that time, the foramen ovale valve M2 closely approaches the atrial septum secundum M1 side by the positioning hold mechanism 60, so that it is possible to pull the foramen ovale valve M2 efficiently. More specifically, for example, in a case in which an aperture between the atrial septum secundum M1 and the foramen ovale valve M2 is relatively large, there is a possibility that only blood is sucked and the foramen ovale valve M2 is not pulled. But here, the foramen ovale valve M2 already closely approaches the atrial septum secundum M1 side, so that it is possible to pull the foramen ovale valve M2 efficiently and it is possible to repress also the excessive suction of blood. There are inter-individual differences for the shapes of the atrial septum secundum M1 and the foramen ovale valve M2, so that there are various kinds of apertures between the atrial septum secundum M1 and the foramen ovale valve M2 mentioned above. However, with the closing device according to the present exemplified embodiment, it is possible to correspond to the variation of the aperture caused by the inter-individual differences. Also, the balloon 40 is positioned at the center of the foramen ovale O, so that it is possible to cover the foramen ovale O suitably by the balloon 40 and it is possible to execute the pulling of the foramen ovale valve M2 caused by the suction more effectively. The balloon 40 can be positioned, as shown in FIG. 17, such that the balloon 40 (the hold surface 42 of the balloon 40) contacts, while extending across or spanning, both the atrial septum secundum M1 and the foramen ovale valve M2).

Next, while maintaining this suction state, the second operation body 75 is returned once and, as shown in FIG. 10B, the first elastic wire 66 and the second elastic wire 67 are straightened out into a straight-line shape and thereafter, the second operation body 75 is operated to move backward and as shown in FIG. 17, the entire positioning hold mechanism 60 is withdrawn by the main tube 63 in the lumen L1 of the catheter 30. Thereafter, while maintaining this suction state, the power supply unit 20A is controlled, a predetermined electric current flows between the electrode portion 41 and the counterpart pole plate 23, and the atrial septum secundum M1 and the foramen ovale valve M2 are mutually fused. When applying electric energy, the electrode portion 41 is positioned at the center of the foramen ovale O, so that it is possible to contact the electrode portion 41 to a suitable position for fusing and so it is possible to execute the fusion efficiently.

When the tissue of the atrial septum secundum M1 and the tissue of the foramen ovale valve M2 are fused, energization is stopped, the first operation body 75 is moved backward, also the balloon 40 which exists at the distal tip of the catheter 30 is housed together with the positioning hold mechanism 60 in the guiding catheter 31, and the guiding catheter 31 is pulled out from the living body.

According to the present exemplified embodiment, the atrial septum secundum M1 and the foramen ovale valve M2 are sucked and held, so that sticking of the foramen ovale valve M2 is not necessary. It is thus possible to decrease the occurrence of bad influence to a treatment portion.

It should be noted that the positioning hold mechanism 60 in the first and the second exemplified embodiments is not limited by the illustrated embodiment mentioned above. For example, FIGS. 18A and 18B illustrate another example of the positioning hold mechanism. As shown in FIG. 18A, it is also possible to provide the first elastic wire 66 and the second elastic wire 67 between the distal tip sleeve body 65 and the distal tip of the main tube 63 without providing the middle sleeve body 64 as in the first and second exemplified embodiments mentioned above. In this illustrative embodiment, when the operation member 7a is moved backward, as shown in FIG. 18B, the second elastic wire 67 is bent and deformed into an arc shape while the first elastic wire 66 is protruded and deformed in an arc shape in the radial direction toward the outside. More specifically, the positioning of the suction and hold portion or the electrode portion to the center of the foramen ovale O caused by the first elastic wire 66 and the holding of the foramen ovale valve M2 caused by the contact member 68 and the distal tip sleeve body 65 which are bent by the second elastic wire 67 are to be performed simultaneously based on one action caused by the backward movement of the operation member 7a.

The present invention is not limited only by aforementioned exemplified embodiments and it is possible for a person skilled in the art to employ various modifications within the technical concept of the present invention. The embodiments described above and illustrated by way of example are discussed in the context of a device used in a treatment for closing a defect of PFO, but the invention is not limited only by this. It is possible to use it in case of closing a passway-shaped defect such as a left auricle closing device (Left Atrial Appendage) or in the case of thermally necrosing a biological tissue in a predetermined region.

The closing devices described here can be utilized to close a defect portion of a PFO relatively simply and safely. The foramen ovale valve can be sucked and pulled relatively easily without sucking blood excessively. Also, the electrode portion can be relatively easily positioned to apply energy at the desired region of the foramen ovale (e.g., center of the foramen ovale).

Having described preferred embodiments of the invention with reference to the accompanying drawings, it is to be understood that the invention is not limited to those precise embodiments illustrated and described, and that various changes and modifications can be effected therein by one skilled in the art without departing from the spirit or scope of the invention as defined in the appended claims.

What is claimed is:

1. A patent foramen ovale closing device for closing a foramen ovale comprising:
   a suction and hold portion at a distal portion of a catheter for sucking and holding tissue of a foramen ovale valve and an atrial septum secundum from one side;
   an electrode portion on a side of the suction and hold portion which contacts the tissue of the foramen ovale valve and the atrial septum secundum;
   a negative pressure supply unit connected to the suction and hold portion for applying negative pressure to the suction and hold portion;
   a hold mechanism operable to protrude from a distal tip of the catheter through forward movement of the hold mechanism for insertion into the foramen ovale and to bend into a position to contact the foramen ovale valve from an other side opposite the one side and press the foramen ovale valve toward the atrial septum secundum;
   an energy supply unit connected to the electrode portion for supplying energy to the electrode portion;
   the foramen ovale valve and the atrial septum secundum being sucked and held by the suction and hold portion in a state in which the foramen ovale valve is pressed by the hold mechanism toward the atrial septum secundum as energy is supplied from the energy supply unit to the electrode portion to fuse together the foramen ovale valve and the atrial septum secundum; and
   a positioning mechanism for positioning the suction and hold portion and the electrode portion relative to the foramen ovale, the positioning mechanism comprising at least one elastic member and a sleeve body, the elastic member having one end operatively connected to an elongated operation member movably positioned in the catheter and an opposite end connected to the sleeve body which is movably mounted on the elongated operation member to permit relative movement between the sleeve body and the elongated operation member, rearward movement of the elongated operation member positioned in the foramen ovale causing the elastic member to outwardly expand into contact with an inner edge of the foramen ovale to position the suction and hold portion relative to the foramen ovale.

2. The patent foramen ovale closing device according to claim 1, wherein the hold mechanism is connected to an elongated operation member movably positioned in the catheter for forward and backward axial movement.

3. The patent foramen ovale closing device according to claim 2, wherein the catheter comprises an axis, and the operation member is rotatable in the catheter centering around the axis of the catheter.

4. The patent foramen ovale closing device according to claim 1, wherein the hold mechanism comprises a part of a positioning hold mechanism for positioning the suction and hold portion and the electrode portion at predetermined positions with respect to the foramen ovale.

5. The patent foramen ovale closing device according to claim 1, wherein the energy supply unit is a monopolar system in which energization is executed between the electrode portion and a counterpart pole plate provided outside of the body.

6. The patent foramen ovale closing device according to claim 1, wherein the electrode portion includes an electrode adapted to contact the foramen ovale valve and an electrode adapted to contact the atrial septum secundum, and the energy supply unit is a bipolar system in which energization is executed between the electrodes.

7. The patent foramen ovale closing device according to claim 1, wherein the suction and hold portion is an expandable and shrinkable expansion portion provided at the distal portion of the catheter, and including a lumen for fluid flow into and out of the expansion portion, the suction and hold portion having a suction and hold surface to which is applied negative pressure by the negative pressure supply unit located on a side of the expansion portion contacting the biological tissue, and the electrode portion is provided on the suction and hold surface.

8. The patent foramen ovale closing device according to claim 1, wherein the suction and hold portion comprises a housing possessing an opening portion to which is applied negative pressure by the negative pressure supply unit on a side contacting the tissue, and the electrode portion is provided at the opening portion.

9. The patent foramen ovale closing device according to claim 8, wherein the hold mechanism passes through the electrode portion.

10. A patent foramen ovale closing device for closing a foramen ovale comprising:
a suction and hold portion at a distal portion of a catheter for sucking and holding tissue of a foramen ovale valve and an atrial septum secundum from one side:
an electrode portion on a side of the suction and hold portion which contacts the tissue of the foramen ovale valve and the atrial septum secundum;
a negative pressure supply unit connected to the suction and hold portion for applying negative pressure to the suction and hold portion;
a hold mechanism operable to protrude from a distal tip of the catheter through forward movement of the hold mechanism for insertion into the foramen ovale and to bend into a position to contact the foramen ovale valve from an other side opposite the one side and press the foramen ovale valve toward the atrial septum secundum;
an energy supply unit connected to the electrode portion for supplying energy to the electrode portion;
the foramen ovale valve and the atrial septum secundum being sucked and held by the suction and hold portion in a state in which the foramen ovale valve is pressed by the hold mechanism toward the atrial septum secundum as energy is supplied from the energy supply unit to the electrode portion to fuse together the foramen ovale valve and the atrial septum secundum;
an elongated operation member movably extending through the catheter, the hold mechanism comprising a bending mechanism to bend a distal portion of the operation member through axial movement of the elongated operation member:
wherein the bending mechanism comprises:
a main tube mounted in the catheter, the operation member being movably positioned in the main tube so as to move axially forward and backward;
a middle sleeve body and a distal tip sleeve body coaxially disposed about the operation member;
at least one elastic wire connecting the distal tip sleeve body and the middle sleeve body;
a contact member attached to a distal tip of the operation member; and
the distal tip sleeve body and the contact member mutually engaging one another by the backward movement of the operation member to deform the elastic wire and bend the operation member.

11. A patent foramen ovale closing device for closing a foramen ovale comprising:
a suction and hold portion at a distal portion of a catheter for sucking and holding tissue of a foramen ovale valve and an atrial septum secundum from one side;
an electrode portion on a side of the suction and hold portion which contacts the tissue of the foramen ovale valve and the atrial septum secundum;
a negative pressure supply unit connected to the suction and hold portion for applying negative pressure to the suction and hold portion;
a hold mechanism operable to protrude from a distal tip of the catheter through forward movement of the hold mechanism for insertion into the foramen ovale and to bend into a position to contact the foramen ovale valve from an other side opposite the one side and press the foramen ovale valve toward the atrial septum secundum;
an energy supply unit connected to the electrode portion for supplying energy to the electrode portion;
the foramen ovale valve and the atrial septum secundum being sucked and held by the suction and hold portion in a state in which the foramen ovale valve is pressed by the hold mechanism toward the atrial septum secundum as energy is supplied from the energy supply unit to the electrode portion to fuse together the foramen ovale valve and the atrial septum secundum;
an elongated operation member movably extending through the catheter;
a middle sleeve body and a distal tip sleeve body coaxially and movably disposed about the elongated operation member; and
at least one elastic wire connecting the distal tip sleeve body and the middle sleeve body.

12. The patent foramen ovale closing device according to claim 11, further comprising a contact member attached to a distal tip of the operation member to move together as a unit with the operation member.

13. A patent foramen ovale closing device for closing a foramen ovale comprising:
a suction and hold portion at a distal portion of a catheter for sucking and holding tissue of a foramen ovale valve and an atrial septum secundum from one side;
an electrode portion on a side of the suction and hold portion which contacts the tissue of the foramen ovale valve and the atrial septum secundum;

a negative pressure supply unit connected to the suction and hold portion for applying negative pressure to the suction and hold portion;

a hold mechanism operable to protrude from a distal tip of the catheter through forward movement of the hold mechanism for insertion into the foramen ovale and to bend into a position to contact the foramen ovale valve from an other side opposite the one side and press the foramen ovale valve toward the atrial septum secundum;

an energy supply unit connected to the electrode portion for supplying energy to the electrode portion;

the foramen ovale valve and the atrial septum secundum being sucked and held by the suction and hold portion in a state in which the foramen ovale valve is pressed by the hold mechanism toward the atrial septum secundum as energy is supplied from the enemy supply unit to the electrode portion to fuse together the foramen ovale valve and the atrial septum secundum;

an elongated operation member movably extending through the catheter;

a main tube extending distally from the suction and hold portion;

the holding mechanism comprising a middle sleeve body and a distal tip sleeve body coaxially and movably disposed about the elongated operation member, and at least one first elastic wire connecting the distal tip sleeve body and the middle sleeve body; and at least one second elastic member connecting the main tube and the middle sleeve body.

* * * * *